(12) United States Patent  
Mayer et al.

(10) Patent No.: US 6,610,186 B1  
(45) Date of Patent: Aug. 26, 2003

(54) METHOD AND DEVICE FOR SEPARATING PARTICLES OR MOLECULES BY MIGRATION THROUGH A FERROFLUID

(75) Inventors: Pascal Mayer, Chemin du Ney (FR); Jérôme Bibette, Bordeaux (FR); Jean-Louis Viovy, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/319,078

(22) PCT Filed: Nov. 28, 1997

(86) PCT No.: PCT/FR97/02149

§ 371 (c)(1),  
(2), (4) Date: Aug. 30, 1999

(87) PCT Pub. No.: WO98/23379

PCT Pub. Date: Jun. 4, 1998

(30) Foreign Application Priority Data

Nov. 29, 1996 (FR) .............................................. 96 14661

(51) Int. Cl.[7] .................. G01N 27/447; G01N 27/453; C02F 1/48
(52) U.S. Cl. ..................... 204/451; 204/455; 204/601; 204/605; 204/647; 204/664; 210/695
(58) Field of Search ................................. 204/450, 451, 204/554, 545, 600, 601, 557, 647, 660, 664, 455, 605; 210/695, 222; 436/526

(56) References Cited

U.S. PATENT DOCUMENTS

| | | | |
|---|---|---|---|
| 3,140,714 A | 7/1964 | Murphy, Jr. et al. | 128/214 |
| 3,477,948 A | * 11/1969 | Inoue | 210/695 |
| 3,941,136 A | * 3/1976 | Bucalo | 607/39 |
| 3,991,743 A | * 11/1976 | Bocalo | 128/843 |
| 4,526,681 A | 7/1985 | Friedlaender et al. | 209/214 |
| 4,911,806 A | 3/1990 | Hofmann | 204/180.1 |
| 5,541,072 A | 7/1996 | Wang et al. | 435/7.21 |

* cited by examiner

*Primary Examiner*—Nam Nguyen  
*Assistant Examiner*—Alex Noguerola  
(74) *Attorney, Agent, or Firm*—Blakely Sokoloff Taylor & Zafman

(57) ABSTRACT

The invention concerns a method for separating particles or molecules whereby these particles or molecules are introduced in a separating medium and a moving force is applied to them in said medium. The method is characterised in that the separating medium is a ferrofluid, i.e. a colloidal suspension of magnetic particles and a magnetic field is applied to this ferrofluid generating therein at least an alternation of a zone rich in magnetic particles and a zone poor in magnetic particles, part at least of the region of the ferrofluid in which this alternation is generated is passed through by the particles or molecules to be separated during their migration.

36 Claims, 7 Drawing Sheets

METHOD AND DEVICE FOR SEPARATING PARTICLES OR MOLECULES BY MIGRATION THROUGH A FERROFLUID

The present invention relates to methods for separating particles or molecules by migration in a separation medium.

A large number of methods are already known in which separation is obtained by applying a motive force within a separation medium to particles or molecules to be separated.

If the motive force is of the electrical type, the situation is referred to as electrophoresis, and if it is of hydrodynamic origin, the situation is referred to as chromatography or filtration.

CONTEXT AND PRIOR ART

Chromatography, filtration and electrophoresis are very widely used for purifying or analyzing molecules or macromolecules, whether synthetic or natural, particles, cells, organelles or viruses. There are large number of ways of implementing these methods, descriptions of which may be found in various works, for example "Chromatographie en phase liquide et supercritique", R. Rosset, M. Caude, A. Jardy, Masson ed., Paris 1991; "Practical High Performance Liquid Chromatography, V. R. Meyer, John Wiley ed. Chichester, N.Y. USA; "Chromatography of polymers", T. Provder ed., ACS publ. Washington D.C., 1993 or "Electrophoresis: theory, techniques and biochemical and clinical applications, A. T. Andrews, Oxford University Press, N.Y. 1986".

However, these techniques have limitations. For DNA, for example, chromatography only allows separation for molecules of relatively small size, and agarose or acrylamide gel electrophoresis is most often preferred to it.

Constant-field electrophoresis does not itself make it possible to separate molecules larger than a few tens of thousands of base pairs (kilobases, Kb), while the intact chromosomes of most cellular organisms, prokaryotic or eukaryotic, and much viral DNA, are several hundreds of kilobases or several megabases (millions of base pairs, Mb) long. Human DNA, for example, has sizes between 50 and 200 Mb. For a large number of applications in medicine and genetics, such as genetic (genome) mapping, variability analysis, cloning with artificial yeast chromosomes, diagnosis, etc., DNA exceeding the separation limits of constant-field electrophoresis needs to be separated as a function of its size.

In order to solve this problem, a new technique known as pulsed field gel electrophoresis has been proposed (PCT WO 84/02001, inventors C. Cantor and D. C. Schwartz, 24.05.84). A large number of variants of this technique has also been developed (see for example EP 0 356 187, EP 0 256 737, U.S. Pat. No. 4,971,671, EP 0 395 315, "Pulsed filed [sic] Electrophoresis", B. Birren, E. Lai, Academic Press, London 1993; "Pulsed filed [sic] Gel electrophoresis", Meth. in Mol. Biol., M. Burmeister and L. Ulanovsky Eds, Humana Press, Totowa, N.J. USA, 1992, and the references cited in these patents and works).

In spite of its significant success, this technique, too, still has drawbacks. The main one is its slowness: it takes several days to separate chromosomes containing several megabases. In addition, since the separation is carried out in a gel, it is difficult to recover the DNA after separation, and this method is poorly suited to preparative applications. Lastly, it remains limited to sizes smaller than 10 Mb.

Electrophoresis can also be used to separate particles of micron or submicron size (colloidal particles, cells, viruses, red blood cells or white blood cells, etc.), as may be necessary in sample analysis, in purification, for diagnosis or for treating certain diseases.

If the particles to be separated have different surface potentials, they can be separated in a liquid medium as a function of this surface potential. Conversely, for a large number of applications it is desirable to separate them as a function of the size of the particles or molecules having the same surface potential. This cannot be done in a liquid medium, and it has been proposed to carry out this type of separation by electrophoresis in very dilute agarose gel, but the particles have a tendency to become trapped in the gel, and these gels are very difficult to handle. Further, this method only works for relatively small particles, typically smaller than one micrometer (G. A. Griess, P. Serwer, Biopolymers, 29, 1863–1866 (1990)). In this case as well, pulsed field electrophoresis makes it possible to extend the range accessible to the method slightly, but in a limited way. Lastly, it should be pointed out that it does not make it possible for particles of similar size to be separated satisfactorily.

In summary, although methods are already known for separating particles, large molecules and in particular DNA, these methods have a large number of drawbacks, linked in particular with their slowness and the difficulties which are encountered with these methods for carrying out the separation of molecules or particles of large size.

One object of the invention is to provide a separation method which does not have these various drawbacks.

Separation methods are already known which employ a combination of electric and magnetic fields in order to separate particles, and in particular DNA.

These methods, referred to as electromagnetophoresis, have been described for example in U.S. Pat. No. 4,726,904 and also in the following publications:

Mukherjee, H. G., majumdar, D., "Fresenius'Z" Anal. Chem., 277, 205 (1975),
O. Lumpkin, J. Chem. Phys. 92, 3848–3852 (1990)
Kowalczuk, J. S., Acta Chromatogr. 1, 34–55 (1992).

In these methods, the magnetic field supplements the electric field to cause migration of the charges to be separated.

U.S. Pat. No. 4,526,681 has already proposed a technique for separating magnetic particles, according to which the particles to be separated are introduced into a ferrofluid medium, to which a magnetic fields [sic] is applied which makes it possible to distribute said particles along a magnetic susceptibility gradient.

However, this technique can only be applied for the separation of magnetic particles having different magnetic susceptibilities.

OBJECTS OF THE INVENTION

For its part, the invention provides a method for separating particles or molecules, in which these particles or molecules are introduced into a separation medium which is a ferrofluid, that is say a colloidal suspension of magnetic particles, and at least one motive force is applied to these particles or molecules within said ferrofluid, characterized in that a magnetic field is applied to this ferrofluid which creates in it at least one alternation of one (or more) zone(s) rich in and a zone lean in magnetic particles that the particles or molecules pass through during their migration, which brings about their separation.

A method of this type makes it possible to separate the particles or molecules as a function of the speed at which they move within the ferrofluid, and performs better than the methods known to date in terms of separation speed and/or in terms of the size range in which the separation can be carried out.

It will be noted that the method proposed by the invention makes it possible to separate essentially nonmagnetic particles (minimal or zero magnetic susceptibility).

The motive or migration force used is generally nonmagnetic.

In a preferred embodiment of the invention, which is particularly advantageous for the separation of particles carrying an electric charge, the migration force is obtained by applying an electric field within the separation medium. The method then constitutes an electrophoresis method.

It will in general be advantageous to choose as the separation medium a ferrofluid whose magnetic particles are essentially neutral, so that they will not be moved under the action of the electric field. However, certain particular applications may nevertheless require magnetic particles of given charge, if it is desired for example to decrease or increase the interaction of the particles to be separated with the particles.

In a preferred embodiment, which may or may not be combined with the preferred embodiments described above, the magnetic field is essentially perpendicular to the direction of motion of the particles.

Two embodiment versions which are moreover preferred, and may be combined with any one of the embodiments described above but are mutually exclusive, consist in using a magnetic field:

a) which is essentially constant in the zone where it is applied, b) which has an intensity gradient in the zone where it is applied.

Similarly, two embodiment versions which may be combined with any one of the embodiments described above but are mutually exclusive, consist in using:

c) a separation zone which has a thickness which is essentially constant in the direction of the magnetic field, this thickness being chosen, with the concentration of the magnetic particles in the separation fluid and the amplitude of the magnetic field, as a function of the dimensions of the particles or molecules to be separated; in particular, larger thicknesses are preferably used for particles and molecules of larger size;

d) the separation zone has a variable thickness along the preferential migration direction of the particles or molecules to be separated, the thickness of this zone being chosen, with the concentration of the magnetic particles in the separation fluid and the amplitude of the magnetic field, as a function of the dimensions of the particles and molecules to be separated; in particular, larger thicknesses are preferably used for particles and molecules of larger size.

The methods according to paragraphs a) and c) are preferably used to obtain a high resolution over a relatively small range of sizes, while the methods according to paragraphs b) and d) are better suited to separations in a large range of sizes.

In a particularly simple embodiment variant of paragraph d), the walls of the separation zone which are essentially perpendicular to the magnetic field are slightly inclined relative to one another, giving said zone a "wedge" shape.

In the favored embodiments described above, the best results are most often obtained when the average dimension of the separation zone in the direction parallel to the direction of the magnetic field is between 1 micrometer and 1 mm, and preferably between 10 micrometers, and 100 micrometers.

This method is advantageously implemented with the various following steps:

filling the separation zone with the separation medium;

activating the magnetic field;

introducing a certain quantity of a sample containing the particles or molecules to be separated on one side of the separation zone;

activating means exerting a motive force on the particles or molecules to be separated.

It should be noted that the order in which these steps are listed corresponds to a favored embodiment of the invention, but that it is equally possible in the scope of the invention to implement them in a different order, for example by activating the magnetic field after the introduction of the samples to be separated, and/or by activating rather the motive force.

In the scope of the invention, detection or observation of the passing of the separated products and/or collection of the separated products may be implemented at the outlet of the separation zone.

Advantageously, in addition, the ferrofluid is automatically replaced between two separation operations.

The invention is particularly advantageous for the separation of particles or macromolecules of large size, such as nucleic acids and particularly DNA, and yet more particularly DNA molecules of size between 50 Kb and several hundreds of Mb. It is also particularly advantageous for the separation of objects in suspension in a liquid, such as cells, viruses, nonmagnetic colloidal suspensions and liposomes. These examples should not however be interpreted as a restriction of the field of the invention, which may also in certain cases prove advantageous for the separation of other types of objects like, here again given by way of nonrestrictive examples, proteins and synthetic or natural macromolecules.

A further object of the invention is to provide a device for the separation of particles or molecules which comprises a cell that receives a separation medium, which is a ferrofluid, that is to say a colloidal suspension of magnetic particles, means for introducing these particles or molecules into said separation medium and means for applying a magnetic field to this fluid, characterized in that it includes means for applying at least one migration force within said medium and in that, for the application of a magnetic field, there are means capable of creating at least one alternation of a zone rich in and a zone lean in ferrofluid magnetic particles that the particles or molecules to be separated pass through during their migration, which brings about their separation.

The method and the device according to the invention are advantageously used in the scope of a diagnostic method, for separating particles and molecules and, especially but not exclusively, DNA, cells, blood cells or viruses.

They may also be used for obtaining medicines, veterinary or phytosanitary products and cosmetic products, for example including liposomes, proteins, DNA, cells, blood cells, viruses or colloidal suspensions in their composition.

Other characteristics and advantages of the invention will become more apparent from the following description. This description is purely illustrative and does not imply any limitation.

PRESENTATION OF THE FIGURES

This description should be read with reference to the appended drawings, in which.

DETAILED DESCRIPTION

Figure 1:
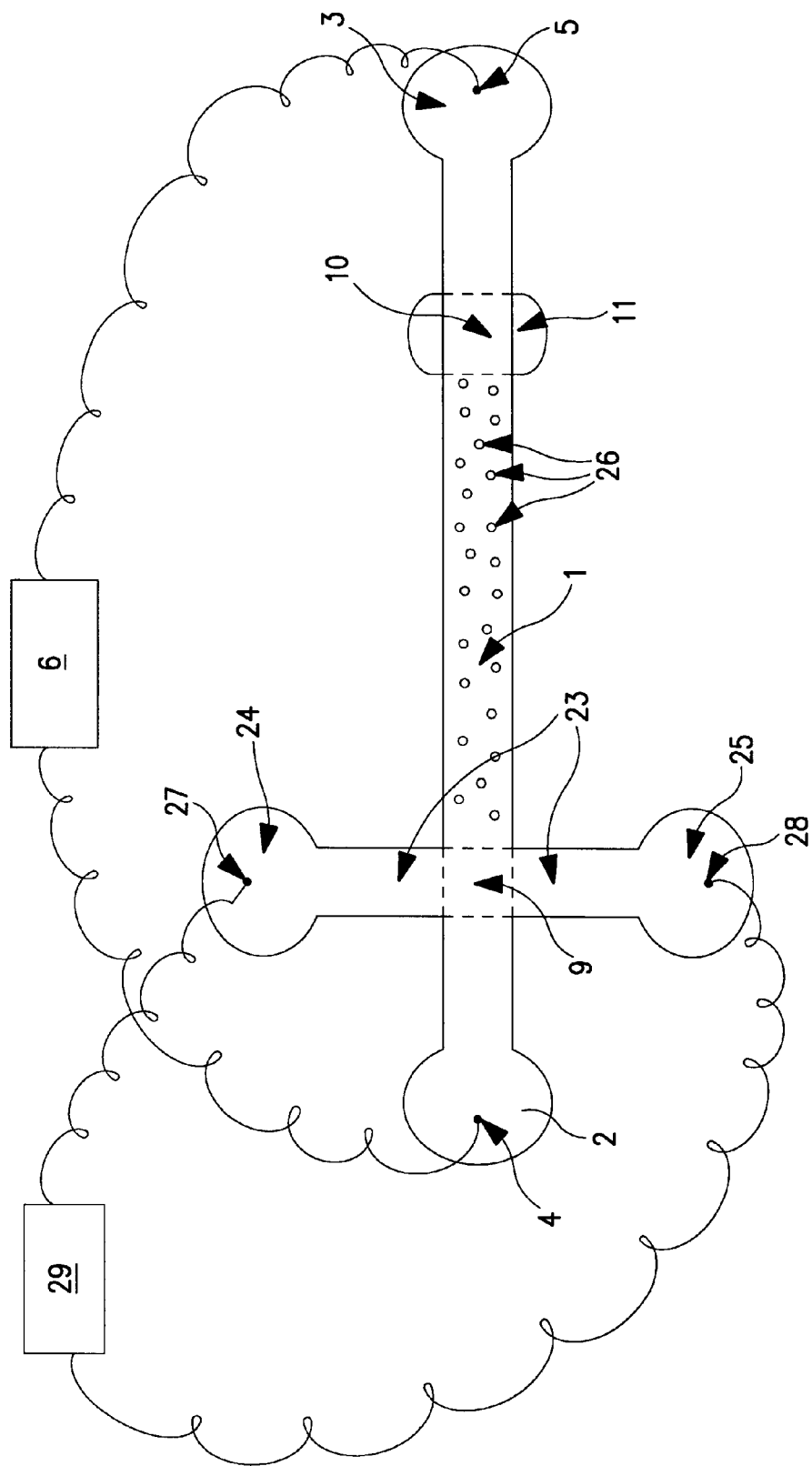
FIG. 1 is a schematic representation in plan view of an example of a device for implementing the invention.
Figure 2:
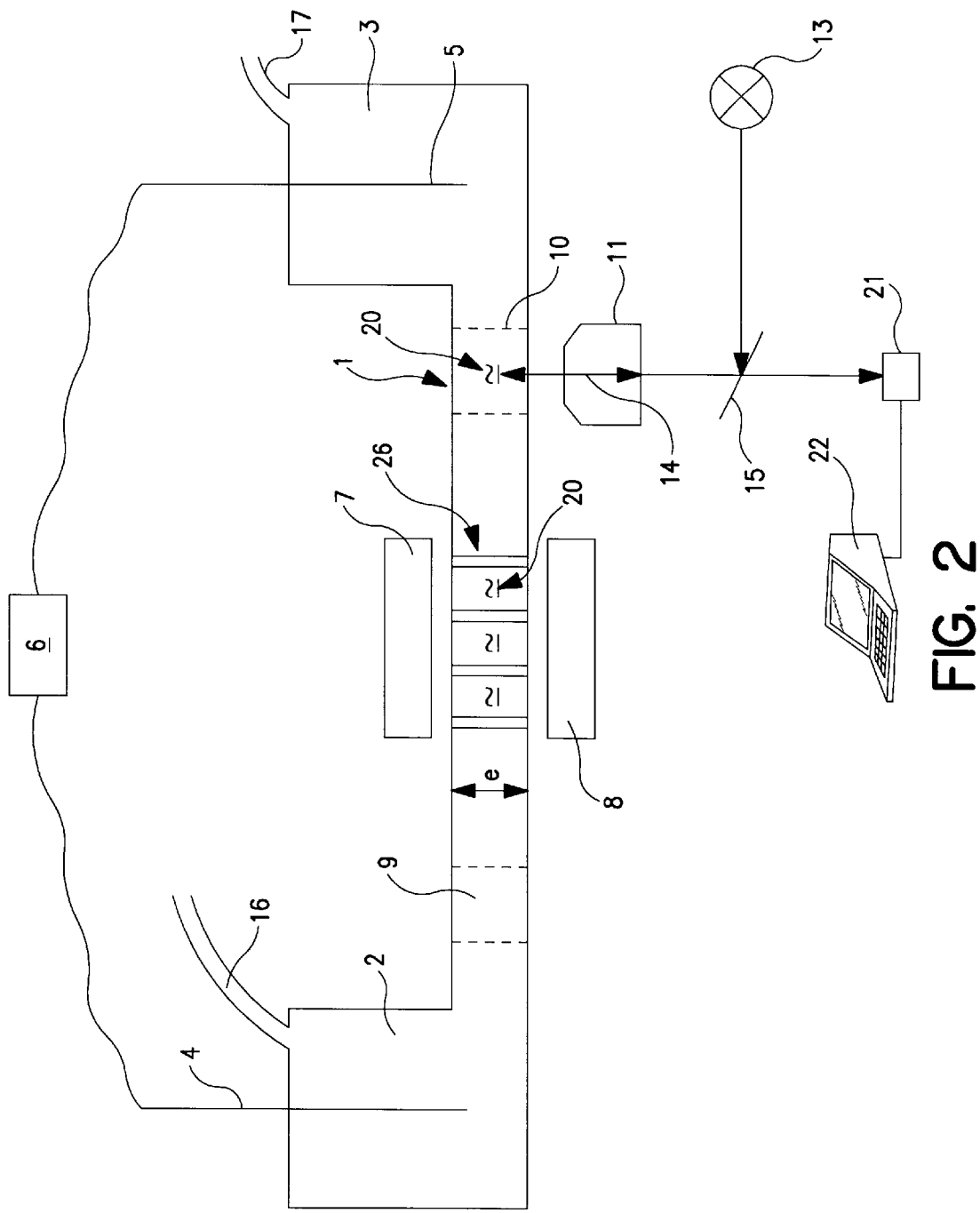
FIG. 2 is a schematic sectional view of the device in FIG. 1.

FIGS. 1 and 2 illustrate a possible device for implementing the invention.

This device comprises an essentially parallelpipedal channel 1 which joins two reservoirs 2 and 3 and into which a ferrofluid, that is to say a liquid containing a colloidal suspension of magnetic particles, is introduced before the separation phase.

This channel 1 constitutes the separation zone.

The device includes means for creating a magnetic field, essentially parallel to the thickness e of said channel, in at least one part of said channel 1.

The effect of this magnetic field is to organize the ferrofluid, in which columns 26 rich in magnetic particles and one or more zones lean in magnetic particles become created. Various means capable of creating such a magnetic field are known to the person skilled in the art, for example Helmoltz coils, electromagnets or permanent magnets.

For most applications, it is advantageous to apply an essentially uniform magnetic field in the separation zone. One simple way of producing such a field, which is schematically represented in FIG. 2, is to place the poles 7 and 8 (respectively North and South) of a permanent magnet or of an electromagnet on either side of the separation channel 1. Another way, schematically represented in FIG. 3, consists in constructing a channel with an axis that is essentially circular and concentric with a Helmoltz coil 37 powered by a current generator (not shown). (All the other elements of the device have functions similar to those described with reference to FIG. 1).

It should, however, be noted that certain applications may require a nonuniform field. The reason for this is that, as is known (E. M. Lawrence et al., Int. J. of Modern Phys. B, 8, 2765–2777, 1994) the size and the spacing of the columns rich in magnetic particles depend on the magnetic field and the thickness of the cell. It is therefore possible to act right away [sic] magnetic as a function of the desired separation.

In a large number of cases, in particular when the particles to be separated are charged, for example if they are polyelectrolytes such as DNA or proteins, cells or viruses, it is advantageous to drive them by means of an electric field essentially perpendicular to the magnetic field used for structuring the separation medium.

To that end, the device includes two electrodes 4 and 5 which are connected to the terminals of a voltage or current generator 6 and are respectively immersed in the reservoirs 2 and 3. Said generator 6 can operate in constant current mode, in constant voltage mode, in constant dissipated power mode, or deliver a current or a voltage having a more complicated profile.

In particular, it may be advantageous in certain cases, and in particular for separating DNA molecules of very large size, to use a voltage whose sense or direction changes repetitively with time, according to the principle of pulsed field electrophoresis, which is well known to the person skilled in the art and is described for example in "Pulsed field Electrophoresis", B. Birren, E. Lai, Academic Press, London, 1993; "Pulsed filed [sic] gel electrophoresis", Meth. In Mol. Biol., M. Burmeister and L. Ulanovsky, Humana Press, Totowa, N.J. USA 1992.

Also in general, the electrode with the same polarity as the particles to be separated is placed on the side of the separation zone 1 via which the sample is introduced, but this arrangement may sometimes be reversed if strong electro-osmosis takes place in the cell, for example if the magnetic particles of the ferrofluid are charged and of the same sign as the particles to be separated.

In order to remove the gases which maybe formed at the electrodes 4 and 5, the reservoirs 2 and 3 are advantageously connected to the free atmosphere or to a common reservoir, either directly or via vents 16 and 17.

The device used for implementing the invention may further optionally include a sample introduction zone 9. One configuration which is advantageous for simultaneously producing the separation zone and the sample introduction zone, consists in obtaining the volume in which the separation takes place by a process of etching or molding on an insulating substrate (for example glass or a plastic) and in using, in order to introduce a well-defined quantity of sample, an auxiliary channel 23 which is etched on the same substrate and is joined to one or more reservoirs or ducts 24, 25, between which it is possible to impose a pressure difference or an electric potential difference, for example using two optional electrodes 27 and 28 powered by a generator 29, as described, for example in A. T. Woolley et al., Proc. Natl. Acad. Sci US, 91, 11348–11352 (1994).

The means for introducing the sample may also, for example, consist:

of one or more indentations or "wells" in which the sample is deposited, as in gel electrophoresis "Electrophoresis: theory, techniques and biochemical and clinical applications, A. T. Andrews, Oxford University Press, N.Y. 1986", or alternatively of a pressurizing or depressurizing system as in capillary electrophoresis, see for example "Capillary Electrophoresis", P. D. Grossman, J. C. Colburn eds, Academic Press, San Diego, Calif., USA, 1992), or alternatively of a channel through which a trickle of sample is poured continuously, as in liquid stream electrophoresis, or alternatively of one of the sample introduction methods employed in chromatography ("Chromatographie en phase liquide et supercritique", R. Rosset, M. Caude, A. Jardy, Masson ed., Paris 1991; "Practical High Performance Liquid Chromatography", V. R. Meyer, John Wiley ed. Chichester, N.Y. USA; "Chromatography of polymers", T. Prodver ed., ACS publ. Washington D.C., 1993).

This list is not, of course, exhaustive.

Similarly, a large number of means capable of detecting the separated products may optionally be combined with the invention, on the side of the channel 1 opposite its inlet (outlet window 10). A large number of detectors employed in chromatography, in electrophoresis or otherwise are known to the person skilled in the art ("Capillary Electrophoresis", P. D. Grossman, J. C. Colurn eds, Academic Press, San Diego, Calif., USA, 1992) and may be used in the scope of the invention: detection by absorption of visible or ultraviolet light, by fluorescent or luminescent emission or irradiation emitted by a radioactive substance, by conductimetry or alternatively by scattering of light, etc.

The embodiment presented in FIG. 2 corresponds to detection by fluorescence; the device includes a source 13 which emits light that can be absorbed by the particles to be detected 20 and is focused by a lens 11 in the detection window 10. Said particles re-emit fluorescent light 14 which has a longer wavelength than the incident light 12 and is split from it by a dichroic filter 15, then is detected by a photosensitive detector 21 optionally connected to an analysis system 22.

The cell may also advantageously, although not necessarily, be equipped, preferably close to its outlet face, with one or more devices intended to collect the various separated products. Such fraction collection systems are known to the person skilled in the art and are already used in chromatography and in electrophoresis. They have not been represented in the figure for the sake of clarity. They may be, for example, a series of tubes collecting the products at various points in the cell, in order to distribute them into various containers (K. Hannig, Electrophoresis, 3, 235–243 (1982)), or conversely a single tube which pours the products leaving the cell at different times into two various containers (see for example R. Grimm, J. Cap. Elec. 2, 111–115 (1995), or alternatively a membrane which moves past close to the outlet of the cell and is capable of adsorbing one or more of the separated products (K. O. Eriksson, A. Palm, S. Hjerten, Anal. Biochem., 201 211–215 (1992)).

Figure 3:
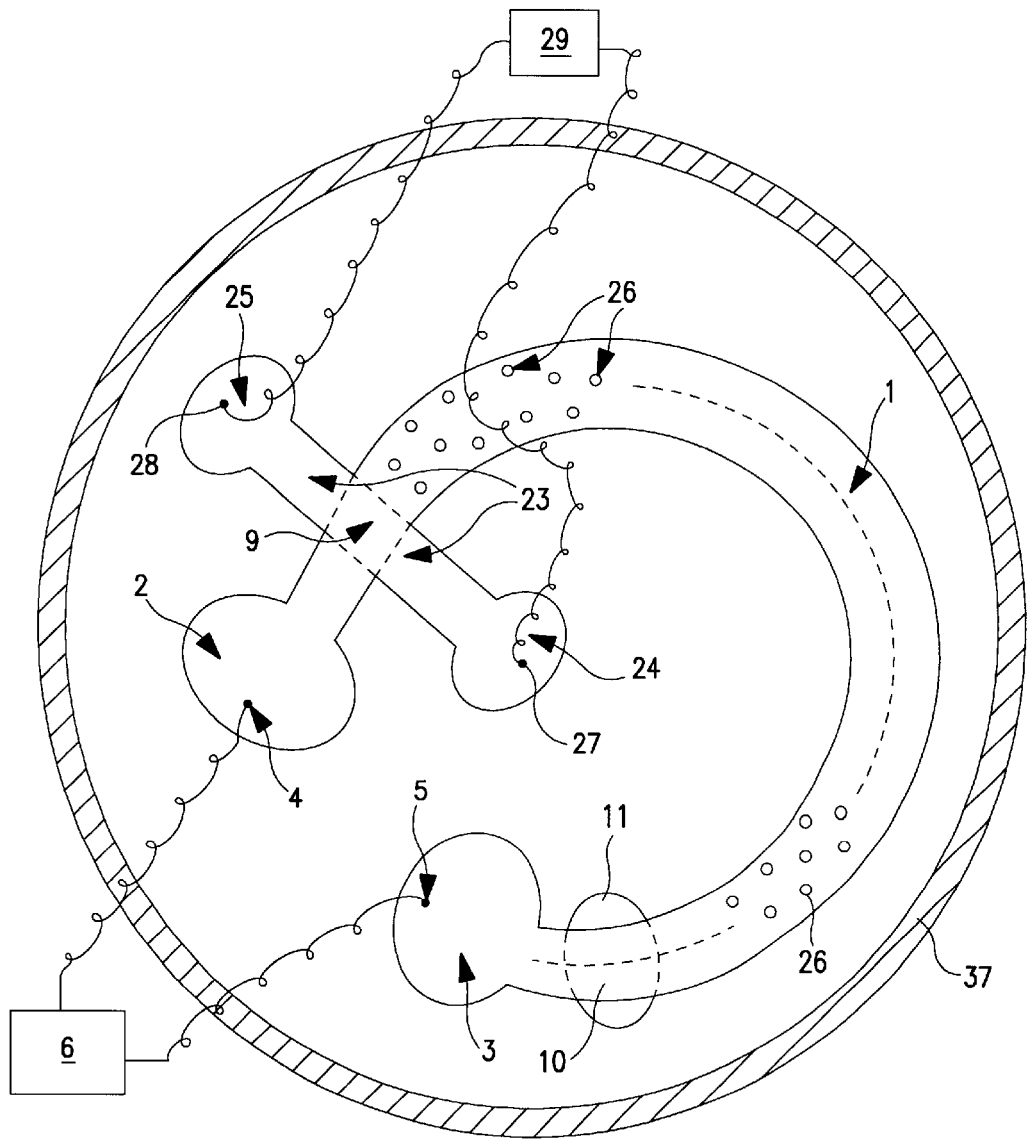
FIG. 3 represents a preferred embodiment of a variant of a device according to the invention similar to the one in FIGS. 1 and 2.
Figure 4A:
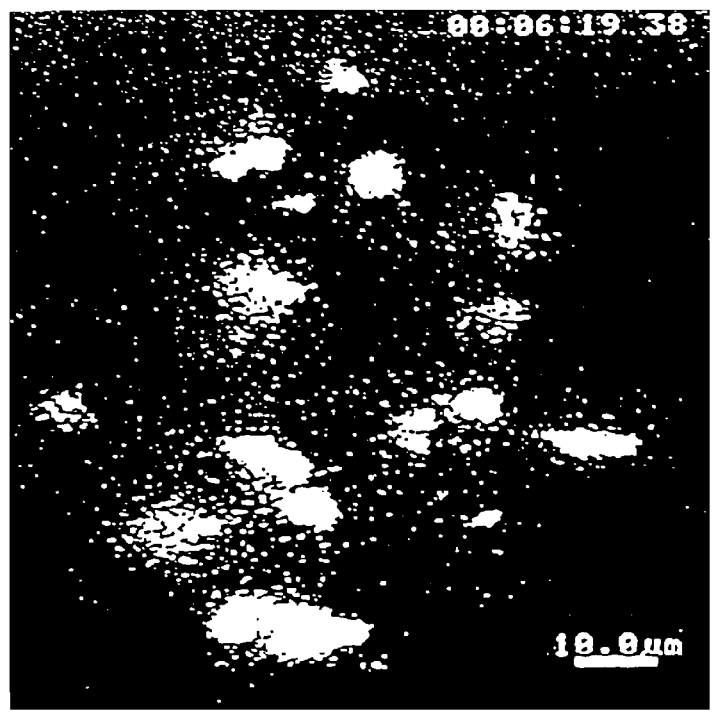
FIGS. 4a to 4d are microphotographs illustrating examples of migration.
Figure 4B:
Figure 4C:
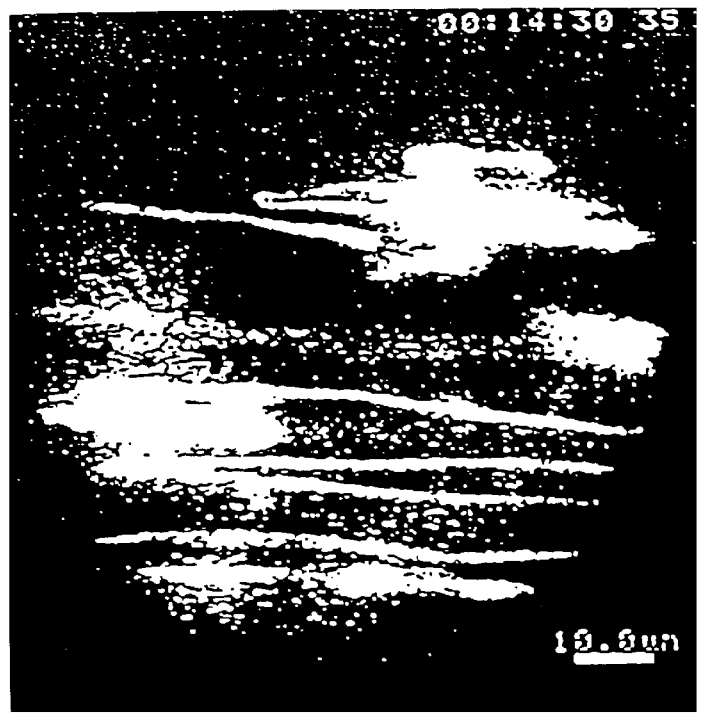
Figure 4D:
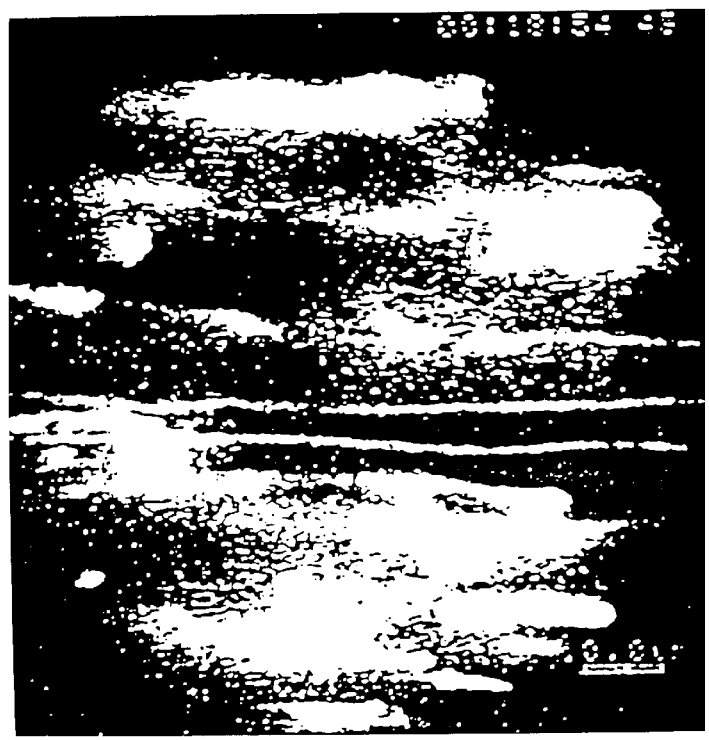

The mode of operation of the invention according to the preferred embodiment presented in FIG. 3 will now be described.

First, the separation zone 1 is filled with a ferrofluid, using for example capillary action or suppression [sic] in one of the reservoirs 2 or 3. The next step involves progressively applying, using the Helmoltz coil 37, a magnetic field sufficient to order the ferrofluid, according to the mechanism described in the aforementioned publication by Lawrence et al. (1994): under the field action, each magnetic particle of the ferrofluid is converted into a micromagnet, and these magnets become grouped together to form regularly spaced columns rich in magnetic particles and parallel to the magnetic field.

The sample containing the particles to be separated, for example DNA molecules, is then introduced. If the sample is of the solid type, such as for example an agarose insert well known to the person skilled in the art, it may simply be placed in the reservoir 25 using a microspatula. If it is liquid, it may be introduced into said reservoir using a micropipette, or using a tube. The next step is to apply slight pressurization between the reservoirs 25 and 24, or an electric potential difference between said reservoirs, using the optional electrodes 27 and 28. Said pressurization or said electric potential difference have the effect of inducing migration of the molecules of the particles contained in the sample from the reservoir 25 to the reservoir 24 via the channel 23, and in particular of leading to the formation of a well-defined sample zone 9 at the inlet of the separation zone 1.

The introduction is then stopped, and the device creating a migration force on the particles to be separated (generator 6, electrodes 7 and 8) is activated. Under the action of this force, the particles to be separated (20) penetrate the separation zone 1. During their migration in this zone, they are separated and the various products initially present in the sample can be identified by their migration time using the detector 21, or can be collected.

An explanatory model of the separation technique which the invention provides will be put forward below. This model is given to assist understanding of the invention and is in no way intended to be exhaustive and restrictive.

During their migration, the particles to be separated which are contained in the sample encounter the columns of magnetic particles, the cohesion of which is ensured by the presence of the field. The particles need to get round these obstacles in order to be transported, and are therefore slowed. It will be understood that this slowing depends on the size of the particles, the largest particles being braked the most.

Various possible mechanisms for such slowing have already been proposed in the context of gel electrophoresis (see for example G. W. Slater et al. Biopolymers 27, 509–524 (1988)) or in that of electrophoresis in microlithographic networks (see for example E. M. Sevick and D. R. M. Williams, Phys. Rev. Lett., 76, 2595–2598 (1996)). However, the invention presents several advantages over these methods of the prior art:

a/ The maximum size of the particles which can be separated is linked with the size of the pores. Within a gel, this pore size is difficult to control, and in particular it is difficult or even impossible to prepare gels having a pore size larger than a few tenths of a micrometer. In the case of microlithography, it is difficult to construct thick cells of more than about 10 microns, which limits sensitivity, flow rate and ease of use. In the scope of the invention, however, by varying the thickness of the cell, the magnetic particle concentration of the ferrofluid and the amplitude of the magnetic field, it is possible to vary at will the distance between the columns, which defines the pore size, and in particular to separate particles of larger size than with a gel. Thus, larger pores and therefore a thicker cell will be chosen in order to separate particles of larger size.

It will therefore be understood that, in order to obtain optimum resolution in a moderate size range, it is beneficial to have a separation zone of constant thickness and a magnetic field of uniform intensity. However, it may also be advantageous for certain applications, in particular when the separation of particles in a large size range is involved, to use a cell of variable thickness, obtained for example by giving a "wedge" shape to the zone in which the separation is carried out.

b/ Since the distance between the obstacles to the progress of the particles to be separated can be rendered at will larger in the scope of the invention than in gel electrophoresis, friction is reduced and the separation speed can be much higher.

c/ In the case of the invention, as in that of microlithography, the obstacles form a well-ordered network with a very uniform repeat unit, which leads to lower velocity dispersion and therefore better resolution than in a gel which has a less regular and uncontrollable structure. In contrast to microlithography, in the scope of the invention it is also possible to vary the size and/or spacing of the obstacles without changing the separation cell itself.

d/ In the scope of the invention, the network of obstacles responsible for the separation can be destroyed and reformed at will, for example in order to use pressurization to remove a contaminated separation medium from the separation cell and replace it with a fresh medium, or in order to avoid the trapping of particles within said medium. In electrophoresis, however, the obstacle network can only be removed from the device manually once it has been formed. Lastly, in lithographic networks, the network of obstacles is permanent, and it can only be replaced by replacing the cell, which considerably increases the running cost, since the manufacturing cost of these cells is very high.

e/ If desired, certain properties of the separation medium such as the rigidity or the dimension of the obstacles may be varied at will during the separation by modifying the magnetic field, while these properties are immutable and uncontrollable in the case of gel or microlithographic network electrophoresis.

f/ Lastly, it may be pointed out that the magnetic particles can be removed very easily from the solution after separation in order to recover a purified product, for example using a magnet, while in the case of a gel, eliminating the agarose requires tricky and more expensive digestion by agarase.

EMBODIMENT EXAMPLE

Preparation of the Ferrofluid Emulsion

The emulsion is prepared using the procedure published by J. Bibette in J. Magn and Magn. Mat. v. 122, p 37 (1993) and J. Coll. and Int. Sci v. 147, p 474 (1991). In short, the emulsion is obtained under shear in a grinder from a 50% (w/w) water-SDS solution, into which a solution of ferrofluids from Rhône Poulenc containing 20 nm $FE_2O_3$ [sic] grains in an oil/$Fe_2O_3$ ratio of 50% (w/w) is progressively incorporated, until reaching a final oil/water ratio of 80% (w/w). This solution is diluted ten times in water. The ferrofluid drops are then sedimented under a magnetic field, the supernatant is taken off and the ferrofluid emulsion is re-suspended in a 0.05% (w/w) solution of Tergitol type NP10 (Sigma)/water. This rinsing operation is repeated four times. The result is a ferrofluid emulsion having an oil/water interface with negligible surface electric charge. Before electrophoresis, this emulsion is supplemented by a TBE buffer solution (45 mM TRIS, 45 mM boric acid, 1.25 mM EDTA, pH 8.3, concentrated 20 times. The final ferrofluid emulsion solution therefore has an oil/water ratio of 8% (w/w) and contains 0.05% (w/w) of NP10, TBE (45 mM TRIS, 45 mM boric acid, 1.25 mM EDTA) at pH 8.3.

Production of the Electrophoresis Cell

The channel 1 is an annular capillary of thickness chosen between 0.01 and 0.05 mm, 4 mm in width and 24 mm in length. It is produced, according to the general scheme presented in FIG. 3, by depositing a film of "parafilm" (American National Cup) stretched manually over a round glass plate of diameter 32 mm and having four perforations passing entirely through it, which respectively fulfil the role of reservoirs 2, 3, 24 and 25. The separation channel 1 and the sample introduction channel 23 are formed by etching on the "parafilm" and are closed by applying a round microscope slide of diameter 30 mm on said film. The cell is sealed by applying previously heated paraffin on its periphery. The cell thus formed is then placed in the magnetic device 37, so that the detection system 11 lies facing a zone 10 of the main channel 1 close to the outlet 3 of the latter, with the filling orifices 2, 3, 24 and 25 on top, and the electrodes 4, 5 (and optionally 27 and 28) are placed in said orifices.

The cell is filled by capillary action with the magnetic emulsion described above, placed in the reservoir 3. A 5 mT magnetic field is progressively applied (200 mT/minute) to the electrophoresis cell placed inside the electromagnet. The axis of the electromagnet coincides with that of the 30 mm circular slide of the electrophoresis cell. This procedure ensures the formation of a regular array of ferrofluid columns whose average spacing, which is a function of the thickness of the cell, is from 0.002 to 0.01 mm (see Lawrence et al. International Journal of Modern Physics B, v. 8, p 2765 (1994). The diameter of the columns can be modulated by the oil concentration of the ferrofluid solution. A transverse channel 23, joining two reservoirs 24 and 25 is used for controlled introduction of the sample. Once the network of columns of ferrofluids have been formed [sic] by setting up the magnetic field, a piece of gel, or a liquid aliquot containing the chromosomes to be separated, (incubated beforehand for at least four hours in a 0.005 mM solution of the YOYO fluorescent intercalating agent (Molecular Probes) if it is desired to carry out detection by fluorescence), is placed in the reservoir 25 and the pressures are allowed to equilibrate in the cell. The transverse channel 23 is then filled with a solution containing the DNA to be separated, by setting up an electric potential difference between the electrodes 26 and 27, or possibly a hydrostatic pressure difference, between the reservoirs 25 and 24; once the channel 23 has been filled, the potential difference between the reservoirs 24 and 25 is terminated and a potential difference (typically a few tens of volts) is applied between the reservoirs 2 and 3, by means of the electrodes 4 and 5 (in the case of separating negative species such as DNA, and in the presence of essentially neutral ferrofluids, the electrode 4 is at the negative potential). This method makes it possible to introduce a well-defined sample volume, corresponding approximately to the center of the cross (volume 9).

Observation of the DNA Molecules During the Electrophoresis

This observation is not necessary for the separation, but it is useful for understanding the mechanisms responsible for said separation. It is carried out with a Nikon Diaphot-TMD-EF epi-fluorescence inverted microscope with an immersion objective having a magnification of 100×, equipped with an image intensifier system (Hamamatsu) connected to a CCD camera and to a display system (Hamamatsu).

The electrophoresis cell described above is mounted on the microscope using a suitable circular support placed inside a cylindrical electromagnet making it possible to obtain 5 mT magnetic fields. The DNA molecules are observed by the fluorescent emission at wavelengths longer than 520 nm from the YOYO (Molecular Probes) intercalated in the DNA molecules and excited by light of wavelength between 450 and 490 nm. The migration of the DNA molecules inside the ferrofluid structure is recorded on video cassettes.

FIGS. 4a to 4d show examples of migration of S. Cerevisae chromosomes. Observing the video sequences clearly shows the following essential points:

the ferrofluid columns are motionless between certain electric and magnetic field limits (here, for a 5 mT magnetic field a voltage of more than 10 V can be applied to the terminals of the capillary).

the DNA molecules penetrate and move between the ferrofluid structures.

the DNA molecules scatter round the ferrofluid columns without any sign of strong interaction (adsorption) and without any sign of significant perturbation to the ferrofluid structures.

the shortest chromosomes (~250,000 base pairs (bp)) retain an essentially spherical configuration on, the observation time scale (40 ms) (4a). This suggests the possibility of separation as a function of molecular mass according to a molecular sieve mechanism, known by the name of "Ogston sieving".

the chromosomes of intermediate size are slowed by the obstacles and temporarily become stretched in the direction of the electric field (4b).

the longest chromosomes observed (4c–4d) are continuously stretched in the direction of the electric field. They form U-, J- and I-shaped structures which are well known in conventional gels. The migration dynamics of these molecules resemble the migration dynamics of DNA molecules of small size (20,000–50,000 bp) in conventional agarose gels. In conventional gels, there is still separation when structures of this type are observed, which suggests that it should be possible, in a continuous field, to separate chromosomes of a size extending at least up to 1,000,000 bp. It is, however, also clear that the use of pulsed field methods should be feasible. Because of the high mobility of the molecules in the ferrofluid structures compared with their mobility in conventional gels, these pulsed field methods in ferrofluid structures should be much faster than in agarose gel.

the ferrofluid structures can be made and unmade at will in the presence of DNA molecules. This allows new separation methods to be envisaged, which are based on coupling between the ferrofluid structure formation dynamics and the DNA deformation dynamics.

it is possible to make the ferrofluid structures mobile, for example by reducing the intensity of the magnetic field or by omitting the steps of washing with Tergitol, i.e. by modifying the surface charge of the ferrofluid droplets. This makes it possible to envisage separation methods based on coupling between the relative mobility of the ferrofluid structures and that of the DNA.

Obtaining Elution Profiles

The microscopy set-up was used here to establish electropherograms (profiles of DNA concentration as a function of time) by integration throughout the image with respect to time. However, other detection devices known to the person skilled in the art could be used to do this.

Figure 5A:
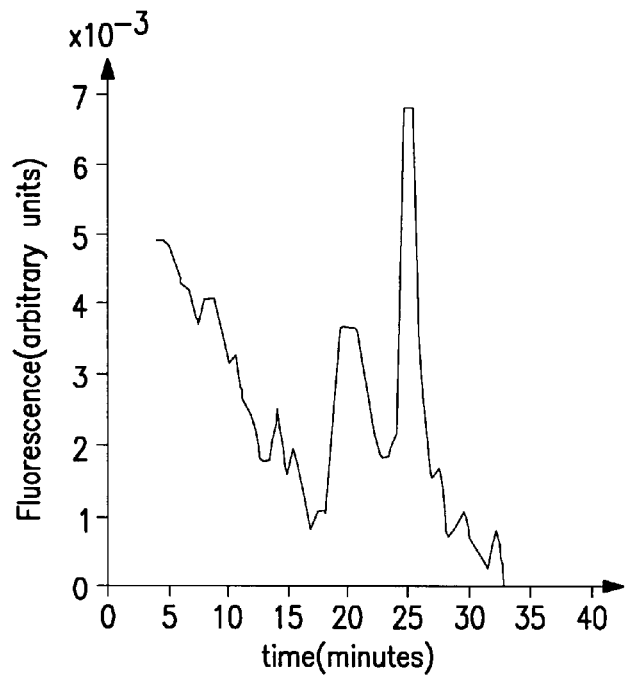
FIGS. 5a and 5b are graphs on which two examples of the variation in the fluorescence at the outlet of a separation device according to the one in FIG. 3 as a function of time have been plotted.

FIG. 5a represents the profile obtained with the injection of a sample containing only lambda phase [sic] DNA at 20 V/cm over a migration distance of 20 mm. The first peak corresponds to degradation products (which are difficult to quantify in gel electrophoresis) and the second peak to the intact chromosomes.

Figure 5B:
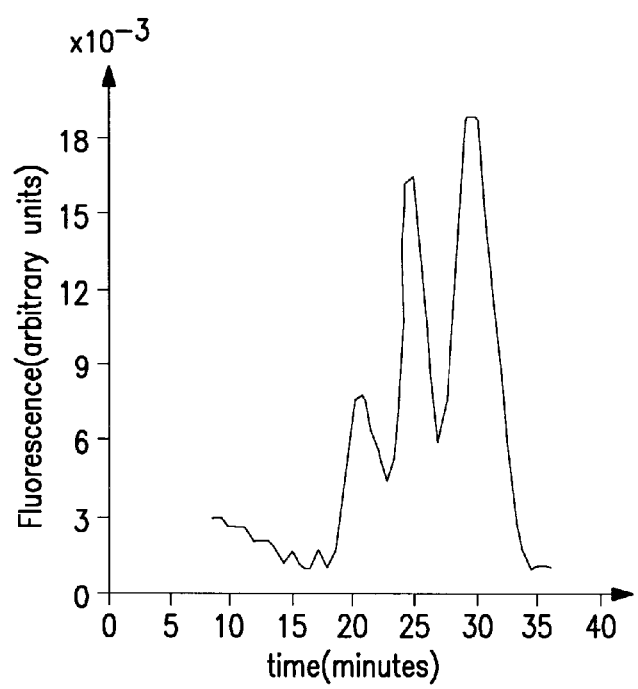

FIG. 5b represents the profile obtained by mixing the sample containing lambda phage DNA (48.5 Kb) and T2 phage DNA (140 Kb). The first two peaks emerge after a time identical to that observed in 5a, and the third peak is that of T2. This separation is obtained in ½ hour, while several hours are necessary with a pulsed field on gel.

Figure 6:
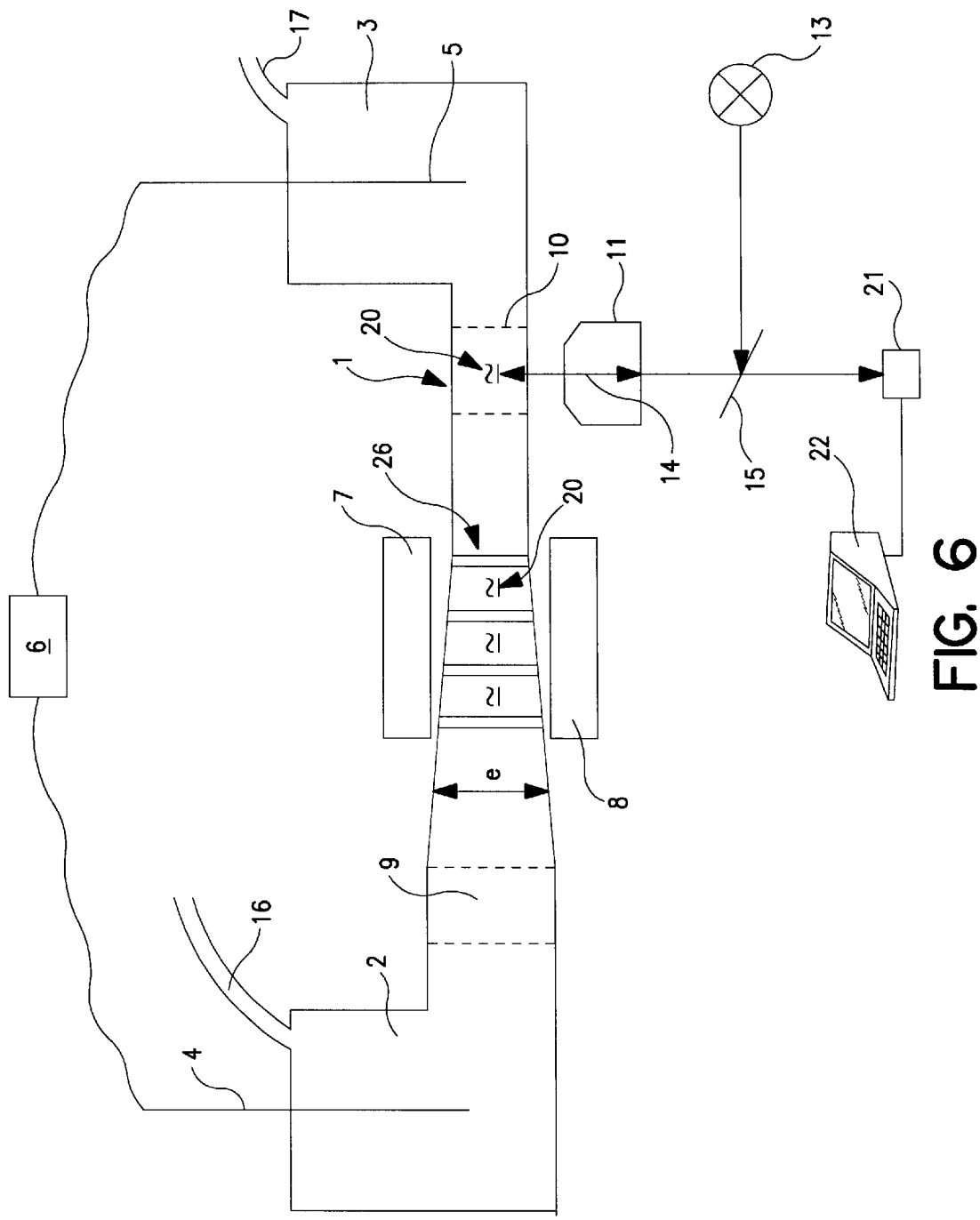
FIG. 6 is a schematic sectional view of the device in FIG. 1.

Another embodiment is illustrated in FIG. 6, which is a possible device for implementing the invention. The device comprises an inclined channel 1 which joins two reservoirs 2 and 3 and into which a ferrofluid, that is to say a liquid containing a colloidal suspension magnetic particles, is introduced before the separation phase. This channel 1 constitutes the separation zone. The device includes means for creating magnetic field, adjacent to the changing thickness e of the channel, in at least one part of said channel 1. The effect of this magnetic field is to organize the ferrofluid, in which columns 26 rich in magnetic particles in one or more zones lean and magnetic particles become created. Various means capable of creating such a magnetic field are known to the person skilled in the art, for example Helmoltz coils, electromagnets, or permanent magnets. For most applications, it is advantageous to apply an essentially uniform magnetic field in the separation zone. One simple way of producing such a field, which is schematically illustrated in FIG. 6, is to place the poles 7 and 8 (respectively north and south) of a permanent magnet or of an electromagnet on either side of the inclined separation channel 1. (All the other elements of the device have functions similar to those described with reference to FIGS. 1 and 2.)

What is claimed is:

1. Method for separating particles or molecules, in which these particles or molecules are introduced into a separation medium comprising a ferrofluid, having a colloidal suspension of magnetic particles and at least one motive force is applied to these particles or molecules within said ferrofluid, wherein a magnetic field is applied to this ferrofluid which creates in it at least one alternation of one zone rich in and one zone lean in magnetic particles of the ferrofluid that the particles or molecules to be separated pass through during their migration, which brings about their separation, wherein the migration force is obtained by applying an electric field within the separation medium, said method constituting an electrophoresis method.

2. Method according to claim 1, wherein the magnetic particles of the separation fluid are substantially neutral.

3. Method according to claim 1 wherein the magnetic field is substantially perpendicular to the direction of motion of the particles or molecules to be separated.

4. Method according to claim 1 wherein the magnetic field is substantially constant in the zone where it is applied.

5. Method according to claim 1 wherein the magnetic field has an intensity gradient in the zone where it is applied.

6. Method according to claim 1, wherein the separation zone has a thickness which is substantially constant in the direction of the magnetic field, this thickness being chosen, as a function of a dimension of the particles or molecules to be separated.

7. Method according to claim 1, wherein the separation zone has a variable thickness along the preferential migration direction of the particles or molecules to be separated, the average thickness of this zone being chosen, as a function of the dimensions of the particles or molecules to be separated.

8. Method according to claim 1, wherein at least two opposite walls of the separation zone are substantially inclined relative to one another.

9. Method according to claim 1 wherein the thickness of the separation zone is between 1 $\mu$m and 1 mm.

10. Method according to claim 9, wherein the thickness of the separation zone is between 10 $\mu$m and 100 $\mu$m.

11. Method according to claim 1 wherein the following steps, are carried out in an arbitrary order:
   filling the separation zone with the separation medium;
   activating the magnetic field;
   introducing a certain quantity of a sample containing the particles or molecules to be separated on one side of the separation zone;
   exerting a motive force on the particles or molecules to be separated.

12. Method according to claim 11, wherein the filing of the separation zone with the separation medium precedes the activation of the magnetic field.

13. Method according to claim 11, wherein at the outlet of the separation zone, at least one of the passing of the separated products is detected and the separated products are collected.

14. Method according to claim 1 wherein the application of the magnetic field precedes the sample introduction.

15. Method according to claim 1 wherein the sample introduction precedes the step of exerting a motive force on the particles or molecules to be separated.

16. Method according to claim 1 wherein the colloidal fluid of magnetic particles is automatically replaced between two separation operations.

17. Method according to claim 1 wherein the molecules separated are nucleic acids.

18. Method according to claim 17, wherein the molecules separated are DNA molecules whose size is between 50 Kb and several hundreds of Mb.

19. Method according to claim 1 wherein the particles or molecules separated are at least one of cells, viruses, non-magnetic colloidal suspensions and liposomes.

20. Method according to claim 1, wherein the particles or molecules to be separated are essentially non-magnetic.

21. Method according to claim 1, wherein the creation of said at least one alternation of zone rich in and zone lean in magnetic particles by means of said magnetic fields is created before the particles of the molecules to be separated encounter said magnetic particles.

22. Method according to claim 1, wherein said at least one alternation of zone rich in and zone lean in magnetic particles is created by assembling in the separation medium a multiplicity of columns rich in magnetic particles which the molecules or particles to be separated encounter during their migration.

23. Method according to claim 22, wherein the columns are substantially parallel to the magnetic field.

24. Method according to claim 22, wherein the columns are regularly spaced.

25. Method according to claim 1, wherein one or several separated particles or molecules are detected.

26. Method according to claim 1, wherein the particles or molecules to be separated are proteins, natural macromolecules or synthetic macromolecules.

27. Device for the separation of particles or molecules, in which the particles or molecules are selected from the group consisting of liposomes, proteins, DNA, cells, blood cells, synthetic macromolecules, natural macromolecules, and viruses, comprising a cell including a separation medium with a ferrofluid having a colloidal suspension of magnetic particles, means for introducing these particles or molecules into said separation medium and means for applying a magnetic field to this fluid, said device further comprising means for applying at least one migration force within said medium and means for creating at least one alternation of a zone rich in and a zone lean in ferrofluid magnetic particles that the particles or molecules to be separated pass through during their migration, which brings about their separation, said device further including means to collect at least one separated particles or molecules.

28. Device for the separation of particles or molecules which comprises a cell that contains a separation medium comprising a ferrofluid, having a colloidal suspension of magnetic particles, means for introducing these particles or molecules into said separation medium and means for applying a magnetic field to this fluid within said medium, wherein said means for applying the magnetic field comprises means for applying at least one migration force within said medium and means for creating at least one alternation of a zone rich in and a zone lean in ferrofluid magnetic particles that the particles or molecules to be separated pass through during their migration, which brings about their separation, said device further including means to detect the separated particles or molecules when they have passed through said alternation, wherein the migration force is obtained by applying an electric field within the separation medium, the device constituting an electrophoresis device.

29. Device according to one of claim 28 or 27 wherein the cell is formed by at least one of etching and molding of an insulating substrate.

30. Device according to claim 28, wherein the thickness of the separation zone is between 1 $\mu$m and 1 mm.

31. Device according to claim 28, wherein the thickness of the separation zone is between 10 $\mu$m and 100 $\mu$m.

32. Method for separating particles and molecules, in which the particles or molecules are introduced into a separation medium comprising a ferrofluid, having a colloidal suspension of magnetic particles and at least one motive force is applied to these particles or molecules within the ferrofluid, wherein a magnetic field is applied to the ferrofluid which creates in it at least one alternation of one zone rich in and one zone lean in magnetic particles of the ferrofluid that the particles or molecules to be separated pass through during their migration, which brings about their separation, wherein at least two opposite walls of the separation zone are substantially perpendicular to the magnetic field and wherein the separation zone has a thickness which is substantially constant in the direction of the magnetic field, the thickness being chosen, as a function of a dimension of the particles or molecules to be separated.

33. Method for separating particles or molecules in which the particles or molecules are introduced into a separation medium comprising a ferrofluid, having a colloidal suspension of magnetic particles, and at least one motive force is applied to these particles or molecules within said ferrofluid, wherein a magnetic field is applied to the ferrofluid which creates in it at least one alternation of one zone rich in and one zone lean in magnetic particles of the ferrofluid that the particles or molecules to be separated pass through during their migration, which brings about their separation, wherein the thickness of the separation zone is between 1 $\mu$m and 1 mm, and an essentially parallelpipedal channel comprises the separation zone.

34. Method according to claim 33, wherein the thickness of the separation zone is between 10 $\mu$m and 100 $\mu$m.

35. Device for the separation of particles or molecules which comprises a cell that contains a separation medium comprising a ferrofluid, having a colloidal suspension of magnetic particles, means for introducing these particles or molecules into said separation medium, and means for applying a magnetic field to this fluid within said medium, wherein said means for applying the magnetic field comprise means for applying at least one migration force within said medium and means for creating at least one alternation of a zone rich in and a zone lean in ferrofluid magnetic particles that the particles or molecules to be separated pass through during their migration, which brings about their separation, said device further including means to detect the separated particles or molecules when they have a passed through the alternation, wherein two opposite walls for the separation zone are substantially perpendicular to the magnetic field, and wherein the separation zone has a thickness which is substantially constant in the direction of the magnetic field, the thickness being chosen as a function of a dimension of the particles or molecules to be separated.

36. Device for the separation of particles or molecules which comprises a cell that contains a separation medium comprising a ferrofluid, having a colloidal suspension of magnetic particles, means for introducing these particles or molecules into said preparation medium and means for applying a magnetic field to this fluid within said medium, wherein said means for applying the magnetic field comprise means for applying at least one migration force within said medium, and means for creating at least one alternation of a zone rich in and a zone lean in ferrofluid magnetic particles that the particles or molecules to be separated pass through during their migration, which brings about their separation, said device further including means to detect the separated particles or molecules when they have passed through said alternation, wherein at least two opposite walls of the separation zone are substantially inclined relative to one another.

* * * * *